United States Patent
McBroom et al.

(10) Patent No.: US 8,721,176 B2
(45) Date of Patent: May 13, 2014

(54) RECHARGEABLE IMAGE DETECTOR SYSTEM AND METHOD

(75) Inventors: Gary Vernon McBroom, Dousman, WI (US); Arturo Eduardo Alcala, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 292 days.

(21) Appl. No.: 13/102,157

(22) Filed: May 6, 2011

(65) Prior Publication Data

US 2012/0281817 A1 Nov. 8, 2012

(51) Int. Cl.
*H01J 31/49* (2006.01)

(52) U.S. Cl.
USPC .......................................... 378/189; 378/204

(58) Field of Classification Search
USPC ................ 378/98.8, 102, 189, 198, 204, 210
See application file for complete search history.

(56) References Cited

U.S. PATENT DOCUMENTS

| | | | |
|---|---|---|---|
| 7,270,477 B1 | 9/2007 | Kari | |
| 7,687,790 B2 | 3/2010 | Utschig et al. | |
| 7,696,722 B2 | 4/2010 | Utschig et al. | |
| 7,852,985 B2 | 12/2010 | Liu et al. | |
| 8,194,823 B2 * | 6/2012 | Ohta et al. | ...................... 378/91 |
| 2006/0067474 A1 | 3/2006 | Schmitt | |
| 2008/0049903 A1 | 2/2008 | Upton | |
| 2010/0246757 A1 | 9/2010 | Liu et al. | |

* cited by examiner

*Primary Examiner* — Jurie Yun
(74) *Attorney, Agent, or Firm* — Fletcher Yoder, P.C.

(57) ABSTRACT

An X-ray imaging system includes a portable cart, a power source disposed on the portable cart, and a detector bin disposed on the portable cart. The detector bin includes a power adaptor configured to adapt power from the power source to power suitable for charging a rechargeable battery, and a first coupling component configured to receive power from the power adaptor. The imaging system also includes a digital X-ray detector configured to be inserted into the detector bin for charging. The detector includes a rechargeable battery, and a second coupling component configured to couple with the first coupling component and transfer power from the first coupling component to the rechargeable battery.

20 Claims, 7 Drawing Sheets

RECHARGEABLE IMAGE DETECTOR SYSTEM AND METHOD

BACKGROUND OF THE INVENTION

The subject matter disclosed herein relates to imaging systems and more particularly to a rechargeable image detector of such systems.

Imaging systems are widely employed in medical environments, such as hospitals. For example, X-ray systems generally are based upon generation of X-rays that are directed toward a subject of interest. The X-rays traverse the subject and impact a film for a digital detector. To provide greater versatility, some detectors are configured as portable devices, in contrast to others that are fixed at a particular location, such as a table or wall stand. In some applications, portable detectors may receive power and communicate data via a cable or tether that connects the portable detector to other components of the imaging system, such as a computer or image processor. While such a tethered arrangement may provide somewhat increased flexibility in the positioning of the detector, in some cases the tether may interfere with the desired positioning and operation of the detector. In other instances, detectors that have an internal battery and communicate wirelessly may also be used. While such wireless detectors may not require a tether for operating power or communication, these wireless detectors may communicate data at a slower rate than some tethered detectors, and may require periodic recharging of their internal batteries, leading to downtime in which the detectors may not be used.

BRIEF DESCRIPTION OF THE INVENTION

In accordance with one aspect of the present disclosure, an X-ray imaging system includes a portable cart, a power source disposed on the portable cart, and a detector bin disposed on the portable cart. The detector bin includes a power adaptor configured to adapt power from the power source to power suitable for charging a rechargeable battery, and a first coupling component configured to receive power from the power adaptor. The imaging system also includes a digital X-ray detector configured to be inserted into the detector bin for charging. The detector includes a rechargeable battery, and a second coupling component configured to couple with the first coupling component and transfer power from the first coupling component to the rechargeable battery.

In accordance with another aspect, an X-ray detector includes a rechargeable battery, a first connector configured to transfer power to the rechargeable battery from a second connector disposed on a portable cart configured to receive the detector, and an isolation circuit coupled to the first connector. The isolation circuit electrically isolates power in the detector from the first connector when the first and second connectors are disengaged.

In accordance with a further aspect, a method for charging a digital X-ray detector includes inserting a portable X-ray detector into a detector bin disposed on a portable cart and coupling a first connector disposed on the detector with a second connector disposed in the detector bin. The first connector is connected to a rechargeable battery disposed in the detector and the second connector is connected to a cart power source disposed on the portable cart. The method also includes supplying power from the cart power source through the coupled first and second connectors to charge the rechargeable battery using a power circuit disposed in the detector.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
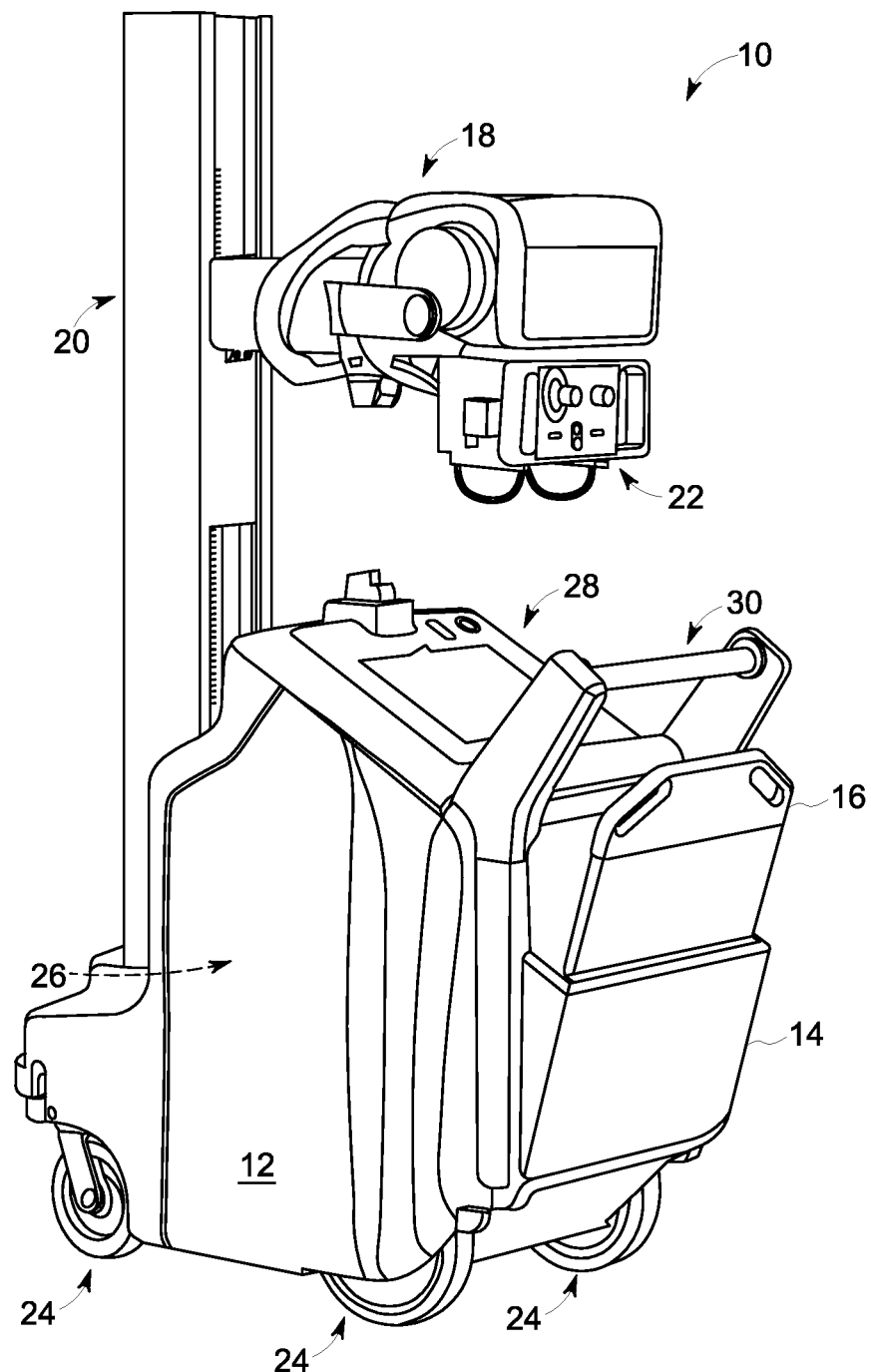
FIG. 1 is a perspective view of an X-ray imaging system, equipped in accordance with aspects of the present technique.

Referring generally to FIG. 1, an X-ray imaging system is represented, referenced generally by reference numeral 10. In the illustrated embodiment, the imaging system 10 may be a digital or analog X-ray system. The imaging system 10 is designed both to acquire original images or image data and to process the image data for display (in a digital X-ray system) in accordance with the present technique.

The imaging system 10 includes a portable cart 12, which enables a user to move the imaging system 10 from one location to another. Attached to the portable cart 12 is a detector bin 14, which may be configured to receive one or more digital X-ray detectors 16. The detector bin 14 is configured to store the detector 16 when the detector 16 is not being used. In addition, various embodiments of the detector bin 14 may be configured to charge a rechargeable battery disposed inside the detector 16, as described in detail below. Charging the battery of the detector 16 while placed in the detector bin 14 may offer several advantages. For example, the time during which the detector 16 is not being used may be utilized instead for charging the battery of the detector 16. In addition, the detector 16 may continue to charge even as the user moves the imaging system 10 about the medical facility. Therefore, the user need not return the detector 16 to a wall or stand mount for charging, which may be located away from the patient or in an inconvenient location. By reducing time associated with transporting the detector 16 back and forth to the wall or stand mount, the user may be have more time for imaging tasks and patient monitoring. Further, the detector 16 may be charged without having to remove a battery from the detector 16. Thus, the detector 16 may remain charged and ready for use.

The portable cart 12 shown in FIG. 1 also includes a support arm 18 that may be vertically moved along a support column 20 to facilitate positioning of a radiation source 22. Further, one or both of the support arm 18 and support column 20 may also be configured to allow rotation of the radiation source 22 about an axis. Further, the portable cart 12 includes wheels 24, which enable the user to move the imaging system 10. The portable cart 12 houses systems electronic circuitry 26 that acquires image data from the detector 16 and that, where properly equipped, may process the data to form desired images. In addition, the systems electronic circuitry 26 both provides and controls power to the radiation source 22 and the portable cart 12 using a power source, such as a battery or transformer. Specifically, the detector bin 14 may include a power adaptor configured to adapt power from the power source to power suitable for recharging the battery of the detector 16. The portable cart 12 also includes an operator workstation and display 28 that enables the user to interact with and operate the imaging system 10. The workstation 28 may include buttons, switches, or the like to facilitate operation of the imaging system 10. Finally, the portable cart 12 may include a handle 30 to facilitate movement of the imaging system 10 by the user.

Figure 2:
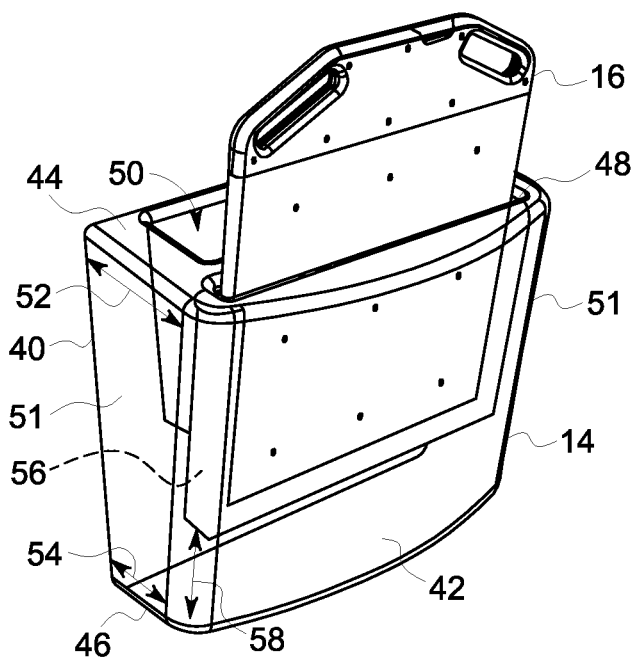
FIG. 2 is perspective view of a detector inserted into a detector bin in accordance with aspects of the present technique.

FIG. 2 is a perspective view of the detector bin 14 of FIG. 1. As illustrated in FIG. 2, the detector 16 is inserted into the detector bin 14. The detector bin 14 includes a back side 40, which is coupled to the portable cart 12 using suitable coupling methods, such as, but not limited to, screws, bolts, adhesives, and so forth. In addition, the detector bin 14 includes a front side 42, which may have a smooth or contoured surface. Further, the detector bin 14 includes a top side 44 and a bottom side 46. The top side 44 may include one or more openings. In the illustrated embodiment, the top side 44 includes a detector slot 48 configured to receive the detector 16. In other words, in certain embodiments, the detector slot 48 may have a rectangular-shaped opening to correspond with the generally rectangular cross-sectional shape of the detector 16. The detector slot 48 may be configured with beveled edges to facilitate insertion of the detector 16 into the detector bin 14. In addition, in some embodiments, the detector slot 48 may include a push open door to help prevent debris or unwanted objects from entering the detector bin 14 when the detector 16 is not in the detector bin 14. In certain embodiments, the detector bin 14 may include more than one detector slot 48 to enable the detector bin 14 to receive more than one detector 16. In some embodiments of the detector bin 14, the top side 44 may include a storage slot 50, which may be configured to store various items that may be used by the user of the imaging system 10. In certain embodiments, the storage slot 50 may not configured to receive the detector 16. For example, the shape of the opening of the storage slot 50 may block insertion of the detector 16. In other embodiments, the storage slot 50 may be configured to receive removable rechargeable batteries for the detector 16. For example, the storage slot 50 may be coupled to the power source to charge spare rechargeable batteries. The detector bin 14 also includes two sides 51, which are coupled to the front and back sides 40 and 42, and the top and bottom sides 44 and 46. In the illustrated embodiment, an upper width 52 of the sides 51 is greater than a lower width 54. Thus, in certain embodiments, the sides 51 may have a tapered appearance. A guide rail 56 is located inside the detector bin 14 and is configured to guide the detector coupling component 76 toward the detector bin coupling component 120 during insertion of the detector 16 into the detector bin 14. The guide rail 56 is coupled to the detector slot 48 for support. In addition, the guide rail 56 may be located a distance 58 above the bottom side 46 of the detector bin 14. The distance 58 may be configured to provide sufficient room for components coupled to the guide rail 56, such as the power adaptor. As described in detail below, such components may be used to charge the detector 16 while the detector 16 is inserted into the detector bin 14.

Figure 3:
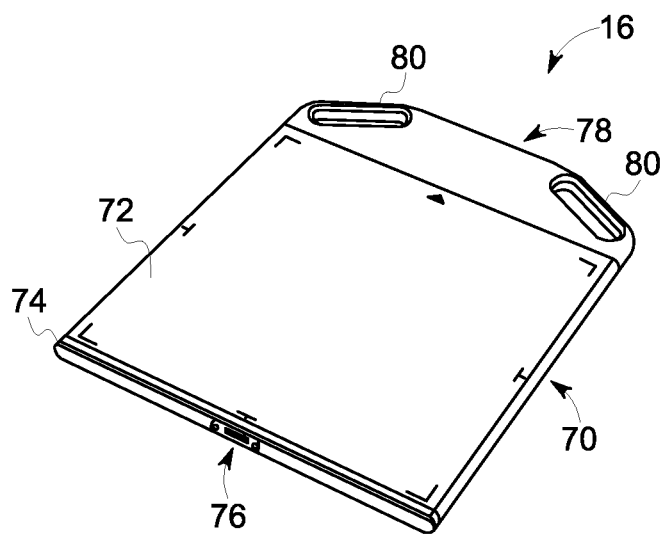
FIG. 3 is perspective view of a detector in accordance with aspects of the present technique.

FIG. 3 is a perspective view of the detector 16 of FIGS. 1 and 2. The detector 16 includes a detector sub-system for generating electrical signals in response to reception of incident X-rays. In accordance with certain embodiments, a shell assembly 70 provides an external enclosure surrounding the detector 16 to help protect internal components of the detector 16 from damage when exposed to an external load or an impact. The shell assembly 70 includes a front side 72 to receive radiation. The shell assembly 70 may be formed of materials such as, but not limited to, a metal, a metal alloy, a plastic, a composite material, or a combination thereof. In certain embodiments, the material used for the shell assembly 70 has a low X-ray attenuation characteristic. Some embodiments may include one or more material compositions having a non-conductive matrix with conductive elements disposed therein, and may provide electromagnetic interference shielding to protect the internal components of the detector 16 from external electronic noise. Additionally, the shell assembly 70 may be designed to be substantially rigid with minimal deflection when subjected to an external load.

In certain embodiments, an end cap 74 may be provided at one end of the detector 16. The end cap 74 may be formed of an impact-resistant, energy-absorbent material such as, but not limited to, nylon, polyethylene, ultra high molecular weight polyethylene, delrin, or polycarbonate. The end cap 74 includes a detector coupling component 76 configured to couple with the detector bin 14 as described in detail below. As shown in FIG. 3, the detector coupling component 76 is located near the middle of the end cap 74. Further, a handle 78 may be mechanically coupled to the detector 16 opposite from the end cap 74 to facilitate portability of the detector 16. The handle 78 may be a separate component, which is attached the shell assembly 70. The handle 78 may be formed of an impact-resistant, energy-absorbent material similar to that used for the end cap 74. The handle 78 may, in turn, include various features that facilitate handling of the detector 16 by the user. In some embodiments, such as that depicted in FIG. 3, the handle 78 may include one or more grips 80, although it is noted that other features, such as contours allowing the user to more easily grip the detector 16, may also or instead be included in other embodiments.

Figure 4:
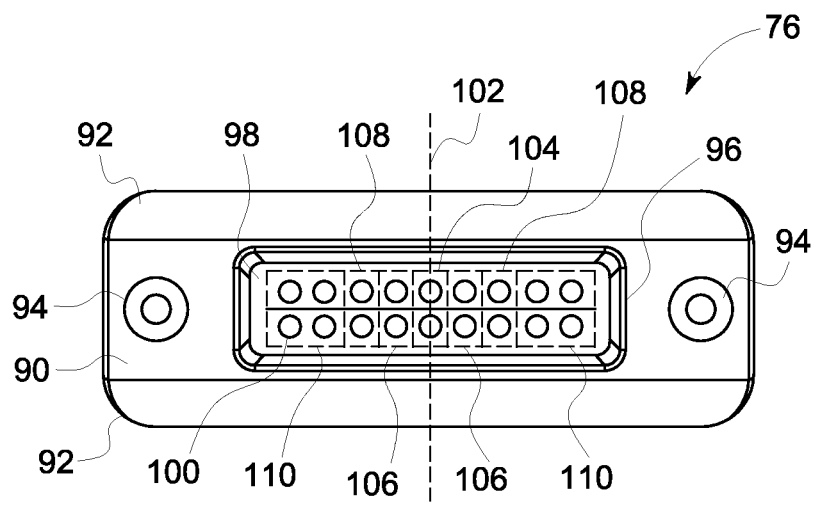
FIG. 4 is an elevational view of a coupling component of a detector in accordance with aspects of the present technique.

FIG. 4 is an elevational view of an embodiment of the detector coupling component 76. The detector coupling component 76 may include a face 90 that is generally flat to match the flat face of the end cap 74. In addition, in certain embodiments, the detector coupling component 76 may include upper and lower faces 92 that are generally curved to match the curved surfaces of the end cap 74. In other words, in certain embodiments, the shape of the detector coupling component 76 may generally match the contours of the end cap 74. The face 90 may include one or more mounting holes 94 to facilitate attachment of the detector coupling component 76 to the detector 16. For example, a screw or similar fastener may be inserted into the mounting hole 94 to attach the detector coupling component 76 to the detector 16. Thus, the mounting hole 94 may enable the detector coupling component 76 to be removed from outside of the detector 16. As show in FIG. 4, the face 90 includes a connector window 96, which may include beveled edges to facilitate coupling with the detector bin 14. Located at the bottom of the connector window 96 is a connector surface 98. Disposed in the connector surface 98 may be one or more connectors 100, which may be made from a conductive material, such as a metal. The connectors 100 may be flush with the connector surface 98.

A longitudinal axis 102 of the detector 16 bisects the detector coupling component 76. As shown in FIG. 4, the connectors 100 are arranged symmetrically about the longitudinal axis 102. For example, detector continuity connectors 104 may be disposed along the longitudinal axis 102. The detector 16 uses the detector continuity connectors 104 to determine what the detector 16 is connected to, as described in detail below. Next, detector power supply connectors 106 may be disposed symmetrically about the longitudinal axis 102 and adjacent to the detector continuity connectors 104. In other words, two detector power supply connectors 106 are disposed on one side of the longitudinal axis 102 and two other detector power supply connectors 106 are disposed on the other side of the longitudinal axis 102. Next, detector power return connectors 108 may be disposed symmetrically about the longitudinal axis 102 and adjacent to the detector power supply connectors 106. The detector power supply and return connectors 106 and 108 may be used to supply 12-volt power to the detector 16 in certain embodiments. Finally, detector data connectors 110 may be disposed symmetrically about the longitudinal axis 102 and adjacent to the detector power return connectors 108. The detector 16 may use the detector data connectors 110 to communicate with a device connected to the detector 16. The symmetric arrangement of the connectors 104, 106, 108, and 110 about the longitudinal axis 102 may enable the detector 16 to connect with the detector bin 14 despite the orientation of the detector 16 when inserted into the detector bin 14. In other words, the detector 16 may be able to connect with the detector bin 14 whether the front side 72 is facing toward or away from the portable cart 12.

Figure 5:
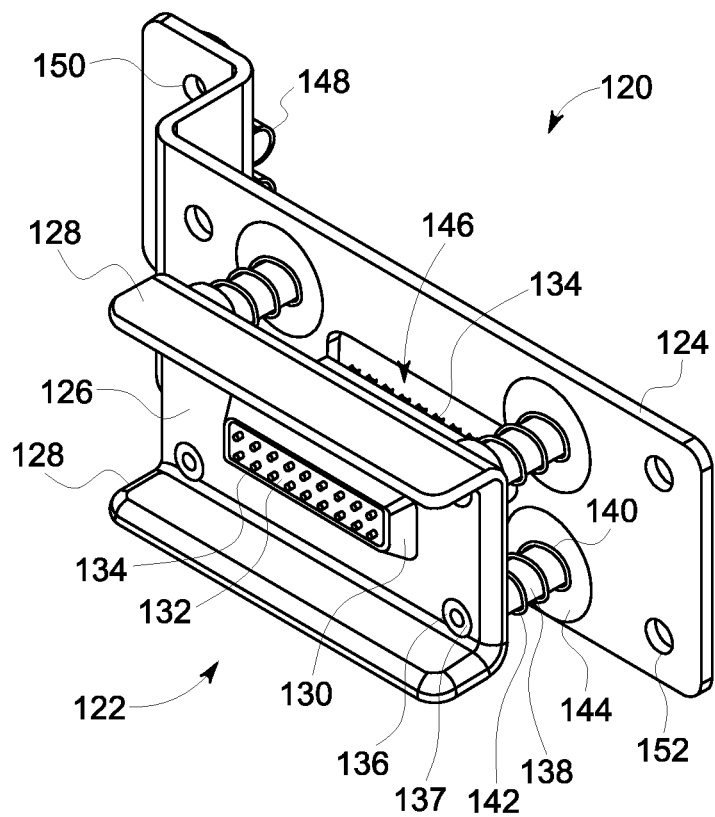
FIG. 5 is perspective view of a coupling component of a detector bin in accordance with aspects of the present technique.

FIG. 5 is a perspective view of an embodiment of a detector bin coupling component 120, which may be attached to the guide rail 56 located inside the detector bin 14. The detector bin coupling component 120 is configured to receive power from the power source located on the portable cart 12, which may be adapted into power suitable for charging the battery of the detector 14 by the power adaptor disposed in the detector bin 14. In addition, the detector bin coupling component 120 is configured to couple with the detector coupling component 76 when the detector 16 is inserted into the detector bin 14 to transfer power to the battery of the detector 14. Specifically, the detector bin coupling component 120 includes an insulator 122 coupled to a base plate 124. In the illustrated embodiment, the insulator 122 includes a face 126 and upper and lower surfaces 128. The face 126 may be generally flat to correspond with the generally flat face 90 of the detector coupling component 76. In addition, the upper and lower surfaces 128 may be configured to fit about the upper and lower surfaces 92 of the detector coupling component 76. The insulator 122 may be made from a generally non-conductive material. Disposed near the middle of the face 126 is a tapered extension 130, which may be configured to generally mate with the connector window 96. In addition, the configuration of the tapered extension 130 and the beveled edges of the connector window 96 may facilitate coupling of the detector coupling component 76 and detector bin coupling component 120 despite any initial misalignment between the coupling components 76 and 120. A seal 132 may be located at the top of the tapered extension 130 to surround one or more connectors 134. The seal 132 may help prevent debris from entering into the insulator 122 and may be made from an elastomeric material. The connectors 134 may be arranged to electrically connect with the mating connectors 100 of the detector coupling component 76 when the detector 16 is inserted into the detector bin 14. In other words, detector bin continuity connectors may couple with the detector continuity connectors 104, detector bin power connectors may couple with the detector power connectors 106 and 108, and detector bin data connectors may couple with detector data connectors 110. In addition, the connectors 134 may be made from electrically conductive materials, such as metals. Further, in certain embodiments, the connectors 134 may be spring pin or pogo style connectors. In other words, the connectors 134 may include internal springs to urge the connectors 134 toward the connectors 100 when the detector 16 is inserted into the detector bin 14.

In certain embodiments, the insulator 122 shown in FIG. 5 may include one or more mounting holes 136 to attaché the insulator 122 to the base plate 124. For example, a screw 137 may be inserted into the mounting hole 136 and configured to mate with a bushing 138 inserted through a mounting hole 140 formed in the base plate 124. A spring 142 may be disposed about the bushing 138 between the insulator 122 and the base plate 124. The bushing 138 may be made from materials such as, but not limited to, aluminum or brass. The spring 142 may be configured to urge the insulator 122 of the detector bin coupling component 120 against the detector coupling component 76 when the detector 16 is inserted into the detector bin 14. In addition, the spring may help to at least partially absorb any forces transmitted from the detector 16 during insertion to help prevent any potential damage to the detector bin coupling component 120. In some embodiments, a washer 144 may be disposed about the bushing 138 between the insulator 122 and the base plate 124. The washer 144 may be disposed against the base plate 124 to help prevent any potential damage caused by contact of the insulator 122 with the base plate 124. The washer 144 may be made from materials such as, but not limited to, delrin. The base plate 124 may also include an opening 146 to accommodate the connectors 134 extending from the back of the insulator 122 when the insulator 122 moves toward the base plate 124. In addition, the opening 146 accommodates wires coupled to the connectors 134. The wires may be restrained by one or more cable clamps 148 coupled to the base plate 124 using one or more cable clamp mounting holes 150 formed in the base plate 124. Finally, the base plate 124 may include one or more mounting holes 152 to enable the detector bin coupling component 120 to be coupled to the guide rail 56 or any other mounting structure provided for in the detector bin 14.

Figure 6:
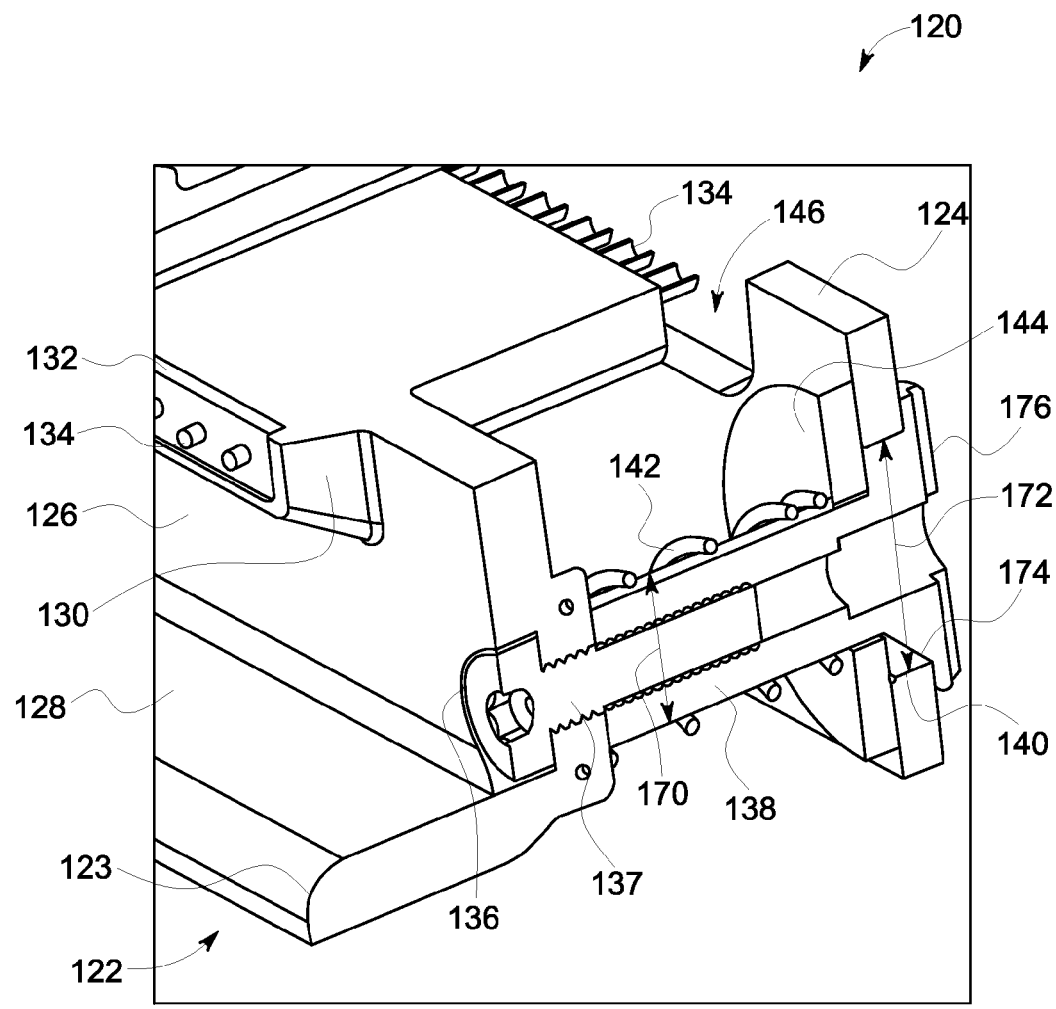
FIG. 6 is cross-sectional perspective view of a coupling component of a detector bin in accordance with aspects of the present technique.

FIG. 6 is a cross-sectional perspective view of the detector bin coupling component 120 that shows certain components in more detail. As shown in FIG. 6, the upper and lower surfaces 128 may include a curved or beveled edge 123 to facilitate mating with the detector coupling component 76. In other words, the beveled edge 123 may help guide the detector coupling component 76 toward the detector bin coupling component 120. In the illustrated embodiment, the connectors 134 extend out the rear of the insulator 122 to be able to connect with the wires described above. The ends of the connectors 134 may be shaped to mate with corresponding holes or slots of a wiring harness. As shown in FIG. 6, the screw 137 fits inside the bushing 138 and may couple to the bushing 138 via a threaded connection. In addition, in certain embodiments, a width 170 of the bushing 138 is less than a width 172 of the mounting hole 140. Further, the bushing 138 includes a centering cone 174 adjacent to the mounting hole 140. The centering cone 174 enables the bushing 138 to be located in a centered position within the mounting hole 140 when the detector bin coupling component 120 is not connected to the detector coupling component 76. When the detector 16 is inserted into the detector bin 14, the centering cone 174 is pushed out of the mounting hole 140, which enables the bushing 138 to float within the larger width 172 of the mounting hole 140. This enables the coupling components 76 and 120 to have at least some freedom of movement during the coupling of the detector 16. Finally, FIG. 6 shows how the insulator 122 may be able to fit at least partially through the opening 146 of the base plate 124 during compression of the spring 142.

Figure 7:
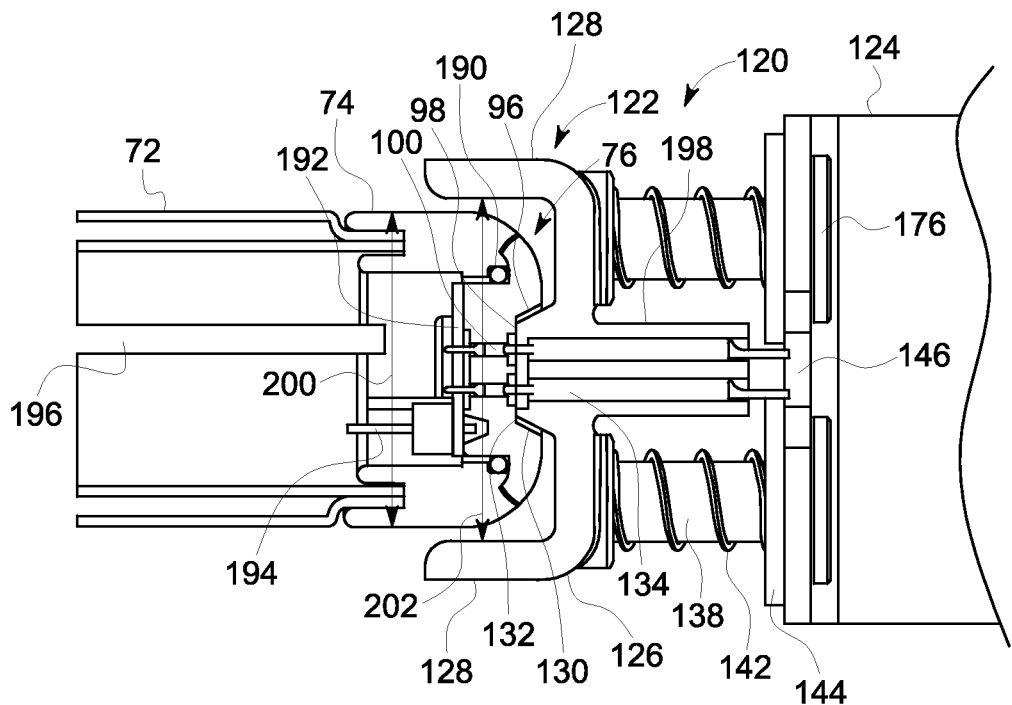
FIG. 7 is cross-sectional view of the coupling components of a detector and a detector bin in accordance with aspects of the present technique.

FIG. 7 is a cross-sectional view of the detector 16 coupled to the detector bin coupling component 120. As shown in FIG. 7, the connector window 96 may be slightly larger than the tapered extension 130 to provide for some freedom of movement in the connection. In the illustrated embodiment, an o-ring seal 190 may be provided between the end cap 74 and the detector coupling component 76 to help prevent debris from entering the interior of the detector 16. In addition, the electrical connectors 100 disposed in the detector coupling component 76 may be attached to a detector circuit board 192 disposed inside the detector 16. One or more wires 194 may be used to couple the systems electronic circuitry 26 with the electrical connectors 100. In addition, a panel support 196 may be disposed inside the detector 16 to support a detector panel used to detect incident X-rays. As shown in FIG. 7, an insulator extension 198 may at least partially enclose the connectors 134 and extend away from the insulator 122. Further, a thickness 200 of the end cap 74 may be less than a height 202 between the upper and lower surfaces 128 of the insulator 122. The difference between the height 202 and the thickness 200 may provide for at least some freedom of movement between the detector 16 and the detector bin coupling component 120. For example, in certain embodiments, the difference between the height 202 and the thickness 200 may be less than approximately 5 mm, 2.5 mm, or 1.5 mm.

Figure 8:
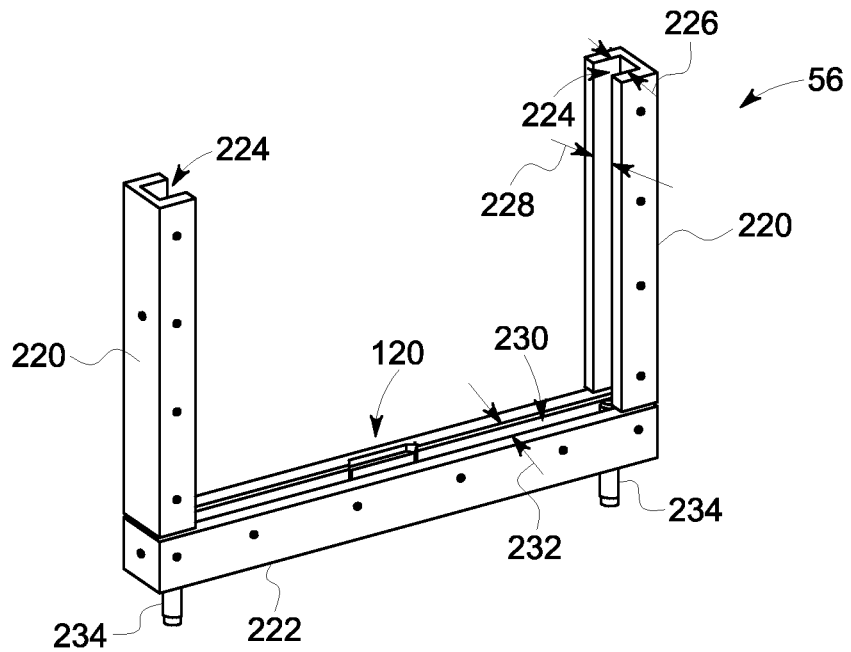
FIG. 8 is perspective view of a guide rail of a detector bin in accordance with aspects of the present technique.

FIG. 8 is a perspective view of the guide rail 56 disposed inside the detector bin 14. The guide rail 56 may include two side rails 220 coupled to a bottom rail 222. The rails 220 and 222 of the guide rail 56 may be made from a low friction material, such as ultra high molecular weight polyethylene or acetyl plastic. The two side rails 220 may include upper openings 224. A width 226 of the upper opening 224 may be greater than a width 228 away from the upper openings 224. The larger width 226 of the upper opening 224 may enable the detector 16 to be initially inserted into the guide rail 56 not completely aligned with the opening of the side rails 220. In other words, the detector 16 may be initially inserted at an angle from the side rails 220. As the detector 16 continues to be inserted into the side rails 220, the detector 16 may gradually become aligned with the side rails 220. The bottom rail 222 may include an opening 230 with a width 232. In certain embodiments, the width 232 may be greater than the thickness 200 of the detector 16 to provide some freedom of motion between the detector 16 and the guide rail 56. In some embodiments, the opening 230 may be configured to provide less freedom of motion than the openings of the side rails 220. As shown in FIG. 8, the detector bin coupling component 120 may be disposed near the middle of the bottom rail 222 to correspond with the position of the detector coupling component 76 near the longitudinal axis 102 of the detector 16. In addition, the bottom rail 222 includes at least two shock absorbers 234 disposed near the side rails 220. In certain embodiments, the shock absorbers 234 may be spring-gas fluid damped plungers. The shock absorbers 234 may be configured to engage the detector 16 when the detector 16 is inserted into the detector bin 14, helping to decelerate the detector 16. In other words, the shock absorbers 234 may be configured to help prevent the detector 16 from damaging the detector bin 14 when inserted or dropped into the detector bin 14. Thus, the shock absorbers 234 may help the coupling components 76 and 120 to securely couple with one another upon insertion of the detector 16 into the detector bin 14. Further, the shock absorbers 234 may help prevent the detector 16 from moving, or bouncing, during movement of the portable cart 12. In other embodiments, the guide rail 56 may include additional shock absorbers 234 and/or shock absorbers 234 locations in different positions along the bottom rail 222.

Figure 9:
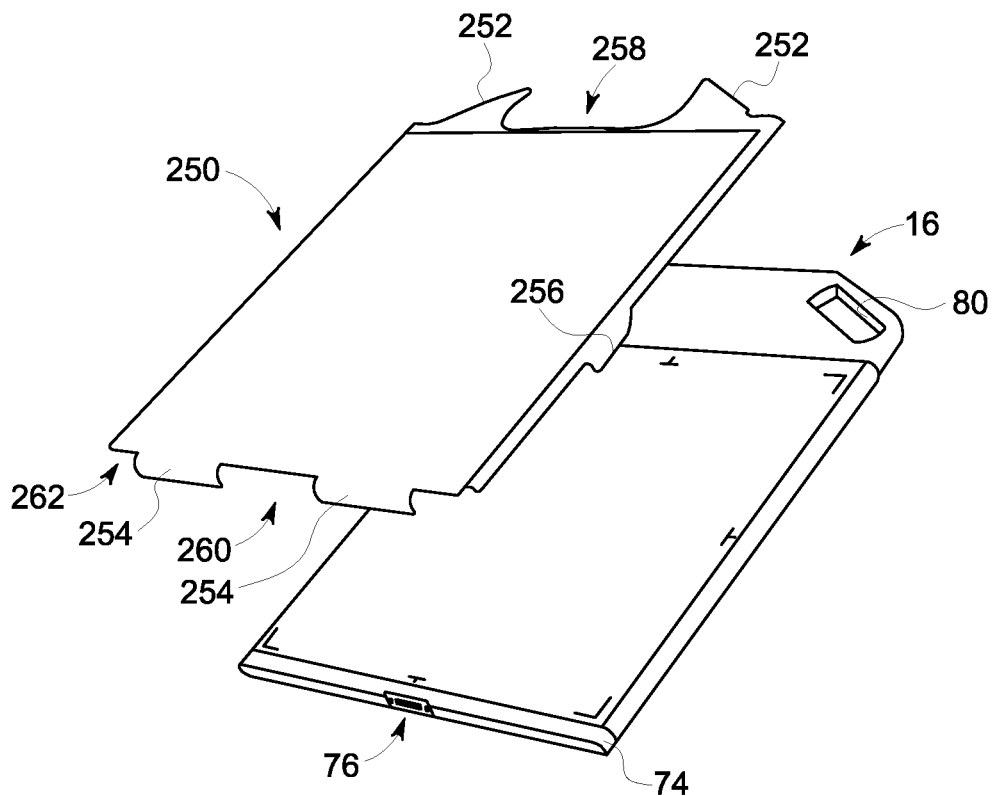
FIG. 9 is perspective view of an anti-scatter grid and a detector in accordance with aspects of the present technique.

FIG. 9 is a perspective view of an anti-scatter grid 250 and the detector 16. The anti-scatter grid 250 may be configured to absorb or otherwise prevent X-ray photons that have been deflected or scattered from impacting the detector 16. To help secure the anti-scatter grid 250 to the detector 16, the illustrated anti-scatter grid 250 includes two handle catches 252 configured to engage the handles 80 of the detector 16. In other words, the illustrated catches 252 are curved portions of the anti-scatter grid 250 configured to engage or snap over the handles 80. Similarly, in certain embodiments, the anti-scatter grid 250 includes two end cap catches 254 configured to engage the end cap 74. In further embodiments, the anti-scatter grid 250 includes two side catches 256 to engage with sides of the detector 16. Thus, the catches 252, 254, and 256 are configured to help maintain, or hold, the anti-scatter grid 250 in place against the detector 16. In other embodiments, other fastening techniques may be used to assemble the anti-scatter grid 250 and the detector 16. In addition, certain embodiments of the detector 16 may omit the anti-scatter grid 250. In some embodiments, the anti-scatter grid 250 includes an upper opening 258 to enable the user to interact with buttons or similar structures located near the handles 80 of the detector 16. Similarly, in other embodiments, the anti-scatter grid 250 includes a coupling component opening 260, or cutout portion, formed between the end cap catches 254. The coupling component opening 260 enables the detector coupling component 76 to mate with the detector bin coupling component 120 when the detector 16 is inserted into the detector in 14. In other words, the coupling component opening 260 of the anti-scatter grid 250 is configured to help prevent the anti-scatter grid 250 from contacting the detector bin coupling component 120.

Figure 10:
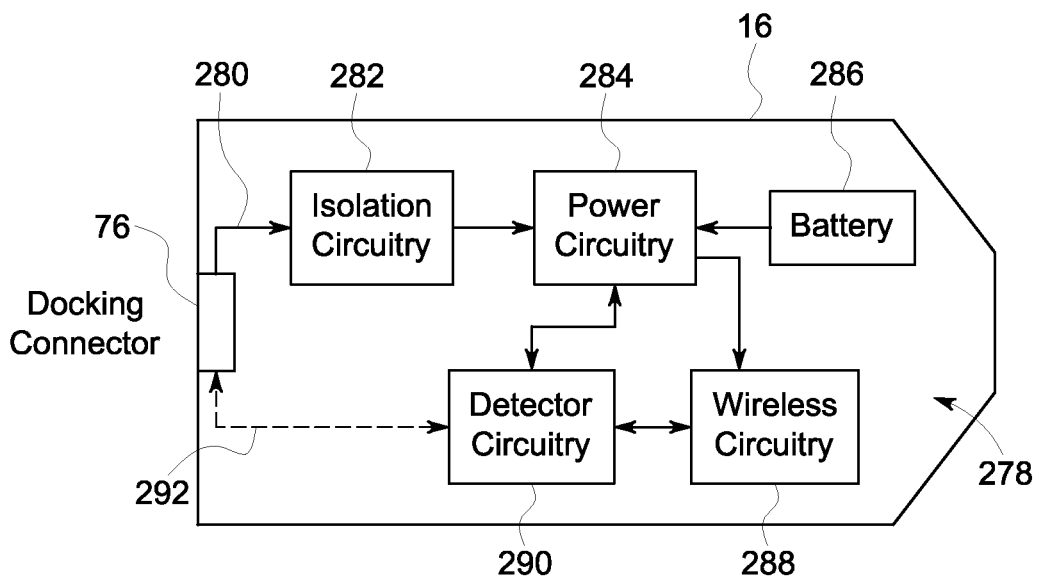
FIG. 10 is diagrammatical overview of a detector in accordance with aspects of the present technique.

FIG. 10 is a diagrammatical representation of the detector 16. Located near the bottom of the detector 16 is the detector coupling component 76, or docking connector. The various components shown in FIG. 10 are disposed in an interior 278 of the detector 16 protected by the shell assembly 70. Electrical power 280 may be transferred from the detector coupling connector 76 to an isolation circuit 282. Specifically, power 280 from the detector coupling connector 76 may be supplied by the systems electronic circuitry 26 of the portable cart 12, which passes through the connectors 134 of the detector bin coupling component 120 and the detector power connectors 106 and 108 of the detector coupling component 76. If the isolation circuit 282 detects power 280, the isolation circuit 282 enables power 280 to pass to a power circuit 284, or power management circuit. However, if the isolation circuit 282 does not detect power 280 (e.g., the detector 16 is not inserted into the detector bin 14), the isolation circuit 282 isolates any source of internal power from the detector 16 from reaching any of the connectors 100. Thus, a user or patient that touches the connectors 100 may be prevented from being exposed to any electrical power. In certain embodiments, the isolation circuit 282 may use one or more relays to isolate internal power from the detector 16 from reaching the detector coupling connector 76. The relays may have a high dielectric breakdown strength. The power circuit 284 is connected to a battery 286, which may be a rechargeable battery configured to supply power to the detector 16 when not connected to a source of electrical power. Thus, the power circuit 284 either sends power 280 to recharge the battery 286 or receives power from the battery 286. In certain embodiments, the power circuit 284 is also used to supply power to a wireless circuit 288 and a detector circuit 290, or imaging circuit. The wireless circuit 288 may enable the detector 16 to communicate wirelessly with other components of the imaging system 10 or any other wireless communication device. The detector circuit 290 may be configured to manipulate the data obtained by the detector 16. In some embodiments, the wireless and detector circuits 288 and 290 are coupled together to enable communication between the circuits 288 and 290. In addition, data 292 may be communicated to and from the detector circuit 290 using the detector data connectors 110 of the detector coupling component 76.

Figure 11:
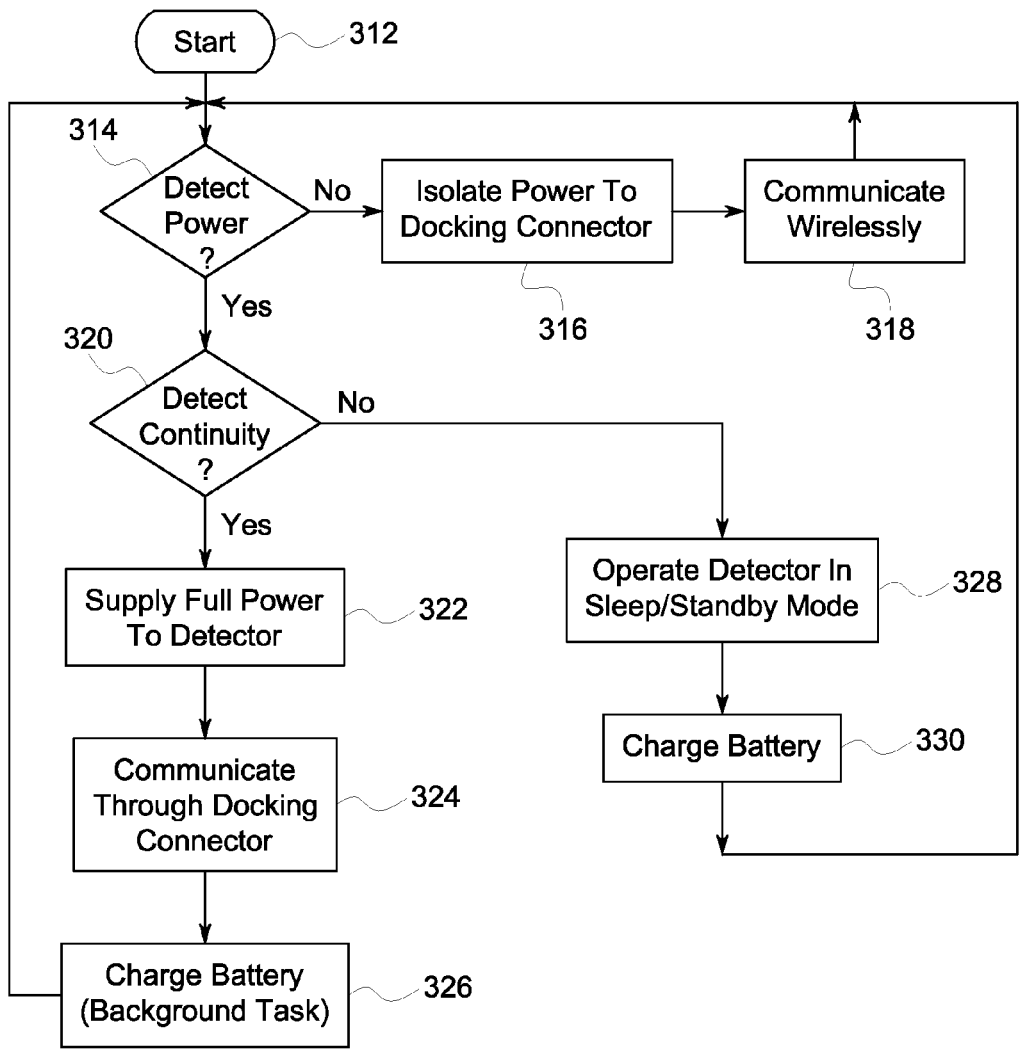
FIG. 11 is flow diagram of a method for operating a detector in accordance with aspects of the present technique.

FIG. 11 is a flow diagram of a method 310 for operating the imaging system 10. The method 310 beings with a start step 312. During the start step 312, the detector 16 may be inserted into the detector bin 14. Next, the method 310 includes using the isolation circuit 282 to detect for power at the coupling component 76 (block 314). If the isolation circuit 282 does not detect power at the coupling component 76 (e.g., the coupling component 76 and the detector bin coupling component 120 are disengaged), the isolation circuit 282 isolates any internal power from the detector 16 from reaching the coupling component 76 to help protect the user and/or patient (block 316). The power circuit 284 may use the battery 286 to power the wireless circuit 288 to enable the detector 16 to communicate wirelessly with other medical devices (block 318). The method 310 then returns to block 314 to repeat the process of detecting for power at the coupling component 76.

Returning to block 314, if the isolation circuit 282 does detect power at the coupling component 76, the detector 16 then detects for continuity at the detector continuity connectors 104 (block 320). For example, the connectors 134 of the detector bin coupling component 120 that are configured to mate with the detector continuity connectors 104 may not be electrically connected to one another. Thus, the detector 16 will not detect continuity at the detector continuity connectors 104 because no current flows through the continuity connectors of the coupling component 76 and the detector bin coupling component 120 that are coupled to one another. On the other hand, connectors of a coupling component disposed in a wall or stand mount, or external charging station, that are configured to mate with the detector continuity connectors 104 may be jumpered, or electrically connected, to one another. Thus, the detector 16 will detect continuity at the detector continuity connectors 104 because of the flow of current through the continuity connectors of the coupling component 76 and the detector bin coupling component 120 that are coupled to one another. In other words, the detector 16 uses the detector continuity connectors 104 to determine whether the detector 16 is placed inside the detector bin 14 or inside a wall or stand mount. If the detector continuity connectors 104 detect continuity, the detector 126 may be located in the wall or stand mount and the detector 16 may use the detector power connectors 106 and 108 to supply the detector 16 with full power (block 322). In addition, the detector 16 may use the detector data connectors 110 to communicate with the wall or stand mount (block 324). Further, the power circuit 284 may supply power to the battery 286 for recharging as a background task (block 326). In other words, priority may be placed on communicating with the wall or stand mount over recharging the battery 286.

If the detector continuity connectors 104 do not detect continuity, the detector 16 may be located in the detector bin 14. Thus, the detector 16 may be operated in a sleep or standby mode (block 328). In other words, the wireless and detector circuits 288 and 290 may be deactivated. In addition, the method 310 includes charging the battery 286 using the power circuit 284 and the detector coupling component 76. In other words, the detector 16 prioritizes recharging the battery 286 when the detector 16 is inserted into the detector bin 14.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray imaging system, comprising:
   a portable cart;
   a power source disposed on the portable cart;
   a detector bin disposed on the portable cart, the detector bin comprising:
      a power adaptor configured to adapt power from the power source to power suitable for charging a rechargeable battery; and
      a first coupling component configured to receive power from the power adaptor; and
   a digital X-ray detector configured to be inserted into the detector bin for charging, the digital X-ray detector comprising:
      a rechargeable battery; and
      a second coupling component configured to couple with the first coupling component and transfer power from the first coupling component to the rechargeable battery;
   wherein the first coupling component comprises first power connectors, first data connectors, and first continuity connectors, and the second coupling component comprises second power connectors, second data connectors, and second continuity connectors, wherein each of the first and second power connectors, the first and second data connectors, and the first and second continuity connectors are configured to couple with one another.

2. The X-ray imaging system of claim 1, wherein the second power connectors, second data connectors, and second continuity connectors are arranged symmetrically about a longitudinal axis bisecting the detector.

3. The X-ray imaging system of claim 1, comprising an isolation circuit disposed in the detector and coupled to the second power connectors, wherein the isolation circuit electrically isolates power in the detector from the second power connectors when the first and second coupling components are disengaged.

4. The X-ray imaging system of claim 3, wherein the isolation circuit comprises a relay.

5. The X-ray imaging system of claim 1, wherein no current flows through the first and second continuity connectors when coupled to one another.

6. The X-ray imaging system of claim 5, comprising a power management circuit disposed in the detector, wherein the power management circuit provides power to the rechargeable battery and removes power from an imaging circuit disposed in the detector when no current flows through the first and second continuity connectors.

7. The X-ray imaging system of claim 1, wherein the first coupling component comprises a spring configured to urge the first coupling component against the second coupling component when the detector is inserted into the detector bin.

8. The X-ray imaging system of claim 1, wherein the detector bin comprises a guide rail configured to guide the first coupling component toward the second coupling component as the detector is inserted into the detector bin.

9. The X-ray imaging system of claim 1, wherein the detector bin comprises a shock absorber configured to engage the detector when the detector is inserted into the detector bin.

10. The X-ray imaging system of claim 1, comprising an anti-scatter grid configured to be coupled to an exterior surface of the detector, wherein the anti-scatter grid is configured with a cutout portion that does not contact the second coupling component.

11. The X-ray imaging system of claim 1, comprising an external charging station configured to receive the detector, wherein the external charging station comprises a third coupling component configured to flow a continuity current through a third continuity connector of the third coupling component and the second continuity connector of the detector when coupled to one another.

12. The X-ray imaging system of claim 11, comprising a power management circuit disposed in the detector, wherein the power management circuit provides power to the rechargeable battery, an imaging circuit disposed in the detector, and a wireless circuit disposed in the detector when the continuity current flows through the first and second continuity connectors.

13. An X-ray detector, comprising:
a rechargeable battery;
a first connector configured to transfer power to the rechargeable battery from a second connector disposed on a portable cart configured to receive the detector;
an isolation circuit coupled to the first connector, wherein the isolation circuit electrically isolates power in the detector from the first connector when the first and second connectors are disengaged; and
a first coupling component configured to flow a continuity current when coupled to a corresponding second coupling component of the portable cart.

14. The X-ray detector of claim 13, comprising a power circuit configured to charge the rechargeable battery and to place the detector in a standby mode when the first and second connectors are coupled to one another.

15. The X-ray detector of claim 14, comprising a wireless circuit configured to enable the detector to communicate wirelessly with a wireless communication device, wherein the power circuit is configured to provide power from the rechargeable battery to the wireless circuit when the first and second connectors are disengaged.

16. The X-ray detector of claim 14, wherein the power circuit is configured to charge the rechargeable battery, provide power to an imaging circuit disposed in the detector, and communicate through the first connector when the detector is placed in a stand configured to receive the detector.

17. A method for charging a digital X-ray detector, comprising:
inserting a portable X-ray detector into a detector bin disposed on a portable cart;
coupling a first connector disposed on the detector with a second connector disposed in the detector bin, wherein the first connector is connected to a rechargeable battery disposed in the detector, and the second connector is connected to a cart power source disposed on the portable cart;
coupling a first continuity connector disposed on the detector with a second continuity connector disposed in the detector bin; and
supplying power from the cart power source through the coupled first and second connectors to charge the rechargeable battery using a power circuit disposed in the detector.

18. The method of claim 17, comprising:
removing the detector from the detector bin to disengage the first and second connectors from one another;
electrically isolating the rechargeable battery from the first connector using an isolation circuit disposed in the detector; and
communicating the detector wirelessly with an external communications device using a wireless circuit disposed in the detector.

19. The method of claim 18, comprising:
inserting the detector into a stand attached to a surface;
coupling the first connector with a third connector disposed in the stand, wherein the third connector is connected to a stand power source connected to the stand;
supplying power from the stand power source through the coupled first and third connectors to charge the rechargeable battery using the power circuit; and
communicating the detector with a stand communications device through the coupled first and third connectors.

20. An X-ray imaging system, comprising:
a portable cart;
a power source disposed on the portable cart;
a detector bin disposed on the portable cart, the detector bin comprising:
a power adaptor configured to adapt power from the power source to power suitable for charging a rechargeable battery; and
a first coupling component configured to receive power from the power adaptor;
a digital X-ray detector configured to be inserted into the detector bin for charging, the digital X-ray detector comprising:
a rechargeable battery; and
a second coupling component configured to couple with the first coupling component and transfer power from the first coupling component to the rechargeable battery; and
an external charging station configured to receive the detector, wherein the external charging station comprises a third coupling component configured to flow a continuity current through a third continuity connector of the third coupling component and a second continuity connector of the detector when coupled to one another.

* * * * *